(12) United States Patent
Keppel et al.

(10) Patent No.: US 6,402,741 B1
(45) Date of Patent: Jun. 11, 2002

(54) CURRENT AND STATUS MONITOR

(75) Inventors: David Keppel, Longmont; Steven H. Johnson; Jim Mageehon, both of Lakewood, all of CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/415,550

(22) Filed: Oct. 8, 1999

(51) Int. Cl.⁷ .............................................. A61B 18/18
(52) U.S. Cl. ............................ 606/34; 606/41; 128/903
(58) Field of Search .............................. 606/30, 31, 41, 606/42, 32–35; 607/66, 67; 600/547, 549; 128/903

(56) References Cited

U.S. PATENT DOCUMENTS

| | | |
|---|---|---|
| 4,005,714 A | 2/1977 | Hiltebrandt |
| 4,452,546 A | 6/1984 | Hiltebrandt |
| 4,514,619 A | 4/1985 | Kugelman |
| 4,630,218 A | 12/1986 | Hurley |
| 4,741,334 A * | 5/1988 | Irnich ......................... 606/35 |
| 4,754,757 A | 7/1988 | Feucht |
| 4,862,889 A | 9/1989 | Feucht |
| 4,942,313 A | 7/1990 | Kinzel |
| 5,167,658 A | 12/1992 | Ensslin |
| 5,318,563 A | 6/1994 | Malis et al. |
| 5,341,807 A * | 8/1994 | Nardella ..................... 600/381 |
| 5,423,808 A | 6/1995 | Edwards et al. |
| 5,430,434 A | 7/1995 | Lederer |
| 5,531,774 A | 7/1996 | Schulman et al. |
| 5,534,018 A | 7/1996 | Wahlstrand et al. |
| 5,540,724 A | 7/1996 | Cox et al. |
| 5,702,386 A * | 12/1997 | Stern et al. ................... 606/34 |
| 5,722,975 A | 3/1998 | Edwards et al. |
| 5,733,281 A * | 3/1998 | Nardella ...................... 606/38 |
| 5,897,552 A * | 4/1999 | Edwards et al. .............. 606/31 |
| 6,063,078 A * | 5/2000 | Wittkampf ................... 606/41 |
| RE36,871 E * | 9/2000 | Epstein et al. ............... 604/67 |
| 6,113,591 A * | 9/2000 | Whayne et al. ............... 606/34 |
| 6,132,429 A * | 10/2000 | Baker .......................... 606/50 |
| 6,142,992 A * | 11/2000 | Cheng et al. ................. 606/34 |

OTHER PUBLICATIONS

Brochure by Richard Wolf Medical Instruments Corp., "Kleppinger Bipolar Forceps & Bipolar Generator", 3pp.
Brochure by Medtrex, "The O.R. Pro 300", 1p.
Brochure by Valleylab, "Valleylab Electroshield Monitoring System", 2 pp.

* cited by examiner

Primary Examiner—Michael Peffley (57) ABSTRACT

An apparatus and method are disclosed for providing visual and audible indications corresponding to the operational status of an electrosurgical generator so that the visual and audible indications can be readily observed and heard within an area normally associated with a working area of a typical operating room. Facilities are provided to mute the audible indication and to indicate that said audible indication has been muted. The indicators preferably include a visual and audible indication corresponding to the RF current delivered by the electrosurgical generator.

18 Claims, 5 Drawing Sheets

CURRENT AND STATUS MONITOR

FIELD

This invention relates generally to current sources and, in particular, to devices for displaying the output and status of current sources.

BACKGROUND

Electrosurgical generators are used by surgeons to deliver electrical energy used, for example, in electrosurgical techniques such as tissue cutting, coagulating small blood vessels, vessel sealing and tissue welding. Radio frequency (RF) power is produced by the electrosurgical generator and applied to the tissue through an electrosurgical tool. RF current is applied utilizing two methods: monopolar, where power is applied to the tissue through a small active electrode and returned through the patient's body to a large return electrode; or bipolar, where power is applied and returned through two small electrodes usually spaced less than a millimeter apart.

Electrosurgical tissue cutting is accomplished by applying an amount of RF current between two electrodes sufficient enough to destroy the tissue. This causes a controlled path of tissue destruction along the electrical path between the electrodes.

The coagulation of small blood vessels is accomplished by applying an amount of RF current which desiccates the tissue to a point where the tissue cells are ruptured and dried but not significantly charred. An application of this technique includes closing small vascular vessels.

Vessel sealing and tissue welding are accomplished by using a suitable electrosurgical tool to grasp and clamp together opposing sides of the wall of a vessel, or two layers of tissue. The opposing sides or two layers are then welded together by applying a controlled amount of RF current, causing a desiccation process where the collagen in the layers of tissue is liquefied so that it cross links between the layers and reforms into a fused mass with a minimum amount of tissue destruction.

It should be noted that each of these techniques requires different amounts and durations of applied RF current. Because these techniques are ultimately dependant on the quantity of RF power applied, in order to achieve successful clinical results during surgery, and to avoid any undesirable tissue damage, it is important that the surgical team should be provided with an indication of the amount of RF current being applied during electrosurgical procedures.

Many electrosurgical generators include various indicators on a front panel. Some have built in current measurement displays. However, electrosurgical generators are normally intended to be small so as not to occupy a large amount of space in the operating room. This results in the indications of the operating status of the generator on the front panel being correspondingly small, and thus potentially not readily visible to all interested members of the surgical team. Also, the electrosurgical generator is usually placed in close proximity to the patient and the surgeon to minimize the length of the electrical connection between the electrosurgical generator and the electrosurgical instruments. This may also result in blocking the indicators from view due to the placement of the operating table, other operating room personnel, etc.

It can be appreciated that it would be desirable to provide a visual and audible indication, external to the electrosurgical generator. An indication of the operational status and the current being generated by the electrosurgical generator, observable by the surgical team, would be beneficial. Also desirable would be an overall indication of the status of the external device providing the indications.

SUMMARY

The forgoing and other problems are overcome by methods and apparatus in accordance with embodiments disclosed herein.

A remote monitor provides a visual indication of the RF current being delivered by an electrosurgical generator. The monitor optionally further provides an audible indication of the RF current being delivered and a means to control the volume of the audible indication, mute the audible indication, and to visually indicate that the audible indicator is muted. The monitor further provides additional visual indications corresponding to the operational status of the electrosurgical generator, and the operational status of the monitor's internal control circuitry. The monitor still further provides the visual and audible indications remote from the electrosurgical generator and provides them in such a way that the visual and audible indications can be readily observed and heard within an area normally associated with a working area of a typical operating room.

DETAILED DESCRIPTION OF THE PREFERRED EMBODIMENT

Figure 1:
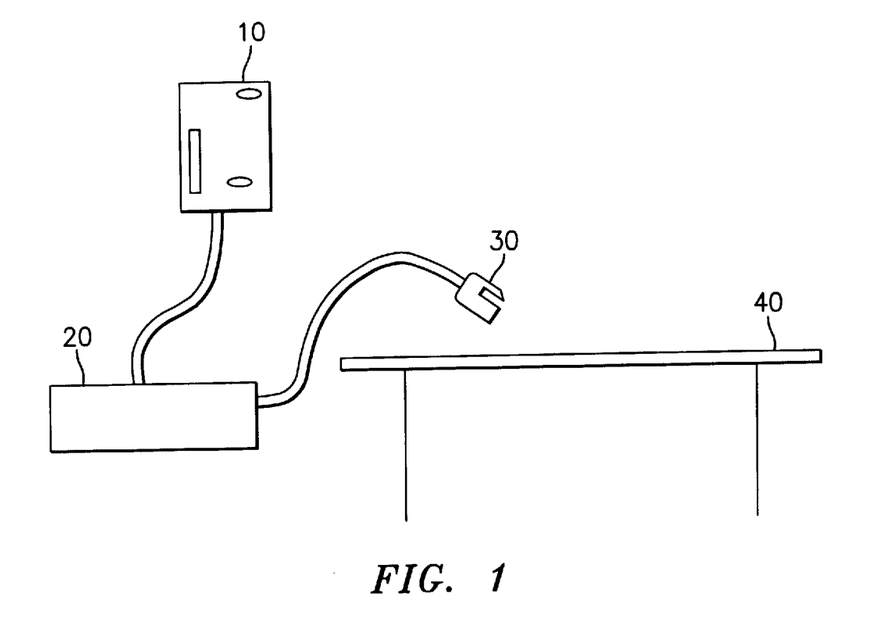
FIG. 1 depicts the monitor coupled to an electrosurgical generator and located within an exemplary operating room.

The monitor 10 is shown in FIG. 1, coupled to an electrosurgical generator 20 and located within the working area of an exemplary operating room. An electrosurgical tool 30 for performing electrosurgery is connected to the electrosurgical generator 20. The electrosurgical tool 30 and the electrosurgical generator 20 are typically located in close proximity to an operating table 40. In accordance with an aspect of this disclosure, the monitor 10 is positioned remotely from the electrosurgical generator 20 at a convenient distance and height so as to be readily observed (and heard) by the surgical team when they are positioned around the operating table 40.

Figure 2:
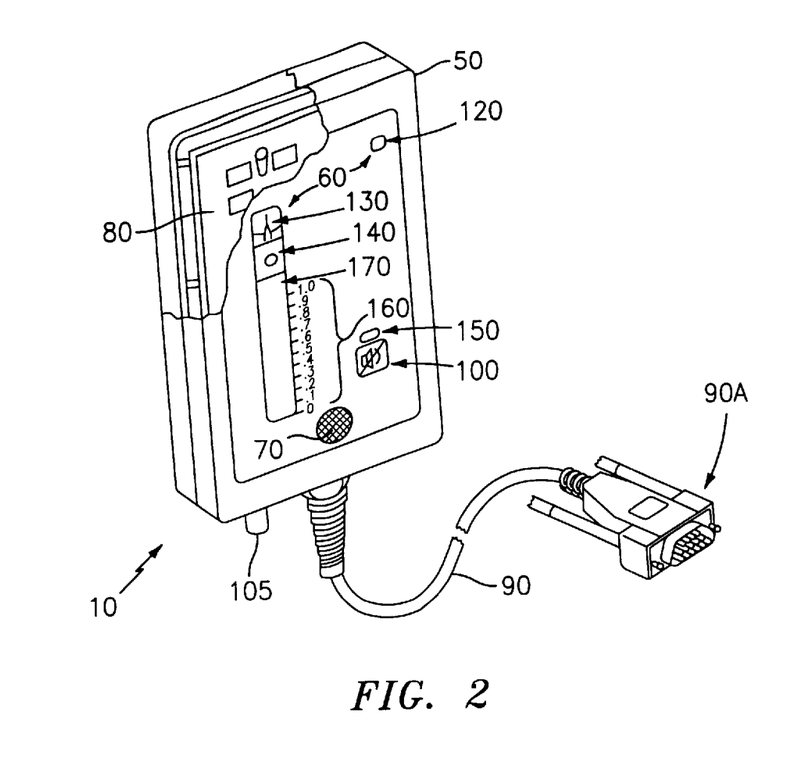
FIG. 2 shows a drawing, partially in cut-away form, of an embodiment of the monitor.

A drawing of an embodiment of the monitor 10 is shown in FIG. 2. An enclosure 50 provides mounting support for the visual indications 60 and at least one audible indicator 70. The enclosure also houses the monitor control circuitry 80. A communications link 90, shown in this figure as a cable, carries signals that indicate the operational status of the electrosurgical generator 20 to the monitor 10. The signals are used for controlling the monitor's visual indications 60 and, in a preferred embodiment, audible indication 70. A mute switch 100 is mounted to the enclosure 50 for causing the monitor control circuitry 80 to silence the audible indication 70. A volume control 105 is also mounted on the enclosure 50 for controlling the volume of the audible indicator 70.

The enclosure 50 is preferably designed so that it provides an appropriate mounting and housing for the various components of the monitor 10, and is further preferably designed to allow the visual and audible indications to be of a size, and to be arranged, to be readily seen and heard by interested personnel within the normal working area of a typical operating room, defined herein as the monitor's working environment. The enclosure 50 is preferably able to be positioned at a location remote from the electrosurgical generator 20 (FIG. 1), and readily mountable on any convenient surface, pole, stanchion or other suitable mounting support. Preferably, the mounting is not permanent, and is instead, temporarily accomplished using, for example, a Velcro® fastener or some other attachment means. The enclosure 50 is further preferably constructed to be easily cleanable and is preferably sealed against external moisture.

The monitor 10 is connected to the electrosurgical generator 20 (FIG. 1) by a communications link. In this embodiment the communications link is preferably implemented as a cable 90 with an appropriate connector 90A. The cable carries signals, reflecting the operational status of the electrosurgical generator 20 (FIG. 1) and optionally carries operational power for the monitor 10, from the electrosurgical generator 20 (FIG. 1), to the monitor 10. The monitor control circuitry 80 utilizes the signals for controlling the monitor's visual indications 60 and in a preferred embodiment, audible indication 70. It is important to note that while the ensuing discussion includes both visual and audible indicators as part of the monitor, it should be realized that in another embodiment, only visual indicators are provided. A detailed explanation of the operation of the monitor control circuitry 80 in response to the input signals is given below. The cable 90 is preferably long enough to allow the monitor 10 to be positioned remotely from the electrosurgical generator 20 (FIG. 1) and to be easily seen and heard within the monitor's working environment. The signals carried by the preferred cable 90, and their functions, are shown in the following table:

| Signal | Function |
| --- | --- |
| +5V | operating power for the monitor |
| RTN HL | operating power ground |
| REGRASP | indicates electrosurgical generator has enabled its REGRASP lamp |
| RF LAMP | indicates electrosurgical generator has enabled its RFLAMP lamp |
| HOST GENERATOR RS-232 TX | serial data communication from the electrosurgical generator |
| ISOLATED GROUND | serial data communication ground |
| RF CURRENT | a voltage in the range of 0–1.2VDC proportional to the amount of current being produced by the electrosurgical generator |
| RTN LL | analog signal return |

In general these input signals provide an indication of the operational status of the generator, which is then redisplayed or repeated, preferably in a more readily observable location or position, relative to the operator of the electrosurgical generator.

It will be recognized by those skilled in the art that the communications link 90 need not be limited to an electrical cable, but may be embodied using any number of communications technologies. For example, a wireless link using radio frequency or infrared signals, or a fiber optic cable could be used, or any other communications technology capable of conveying the desired signals. The communications link 90 need not have the capability to supply operational power to the monitor 10, as the monitor 10 may have its own self contained power supply, for example, a battery or a wall pluggable module.

It should also be noted that the signals need not be carried separately or discretely by the communications link. For example, the communications link could convey a digital bit stream comprising packets of data related to the operational status of the electrosurgical generator 20. The monitor control circuitry could then enable or disable various indicators in response to receiving the bit stream.

The visual indications 60 are preferably implemented as LED's, and are preferably selected to be of a size and brightness that are easily detectable in the monitor's working environment. The LED's 60 preferably are controlled by the monitor control circuitry 80 and provide the following indications.

Referring now to FIG. 2, a Ready LED 120 preferably conveys several indications of the operational status of the monitor control circuitry 80. When the Ready LED 120 is off, it indicates that the monitor control circuitry 80 is not functioning, for example, has no operational power. When flashing, the Ready LED 120 indicates that the monitor control circuitry 80 has passed a particular portion of a self test, explained in detail below, and is waiting for the electrosurgical generator to complete its own self test. When the Ready LED 120 is on in a steady state, it indicates that the monitor control circuitry 80 has passed its self test and its main control program explained below is operational.

A Regrasp LED 130 provides an indication responsive to the REGRASP signal received from the electrosurgical generator 20. The Regrasp LED 130 indicates that the electrosurgical generator 20 (FIG. 1) has enabled its own Regrasp indicator. By way of explanation, the electrosurgical generator 20 enables its own Regrasp indicator when it has detected a condition that suggests disengaging the electrosurgical tool from the vessel or tissue under therapy, and subsequently "regrasping" the tissue or vessel with the electrosurgical tool. This "regrasping" is intended to restore the electrosurgical conditions to an initial state, for example, to correct a shorted electrosurgical instrument.

An RF LED 140 provides an indication responsive to the RF LAMP signal received from the electrosurgical generator 20. The RF LED 140 indicates that the electrosurgical generator 20 (FIG. 1) has enabled its own RF indicator, signifying that RF power is available. The RF LED 140 on the monitor 10 thus relays this condition to the surgical team.

The monitor 10 may be connected to a plurality of electrosurgical generator types. In the event that a particular electrosurgical generator does not provide signals corresponding to the REGRASP or RF LAMP signals, the corresponding Regrasp LED 130 and RF LED 140 do not function and are not illuminated. The Regrasp LED 130 and RF LED 140 are arranged in the enclosure 50 so that their presence is not obvious when they are not illuminated.

The monitor 10 comprises a mute switch 100 that, upon closure, causes the monitor control circuitry to enable or disable the audible indication. When the audible indication is disabled, or muted, the mute LED 150 is illuminated to indicate that while still operational, the monitor 10 is not providing an audible indication (in response to a previous closure of the mute switch 100).

An additional set of LED's 160 are preferably provided to effect a display responsive to the RF CURRENT signal received from the electrosurgical generator 20. A twenty segment, LED display 160 provides a bar graph representation of the RF CURRENT signal, illuminating a segment for each 50 mA of current being delivered by the electrosurgical generator 20, for example, a single segment is illuminated when the RF CURRENT signal represents 50 mA and twenty segments are illuminated when the RF CURRENT signal represents 1.0 A. Preferably, a >1A LED 170 is additionally implemented as part of the display responsive to the RF CURRENT signal. The >1A LED 170 provides an indication in the event that the RF CURRENT signal represents a current being delivered by the electrosurgical generator 20 in excess of 1A.

The >1A LED 170 also provides an additional indication of the operational state of the monitor control circuitry 80. When flashing, the >1A LED 170 indicates that the monitor control circuitry 80 has failed a different particular portion of a self test explained in detail below.

The use of LED's as the visual indications is not to be viewed in a limiting sense upon the practice of this system. Those skilled in the art may recognize that a number of methods and components may be used to create visual indications appropriate for the monitor's working environment in accordance with the teachings found herein.

The audible indicator 70, preferably a piezo-electric speaker, is selected so as to be able to produce about 65 dBa, measured at approximately 1 meter from the speaker, so as to be readily heard by all interested members of the surgical team. The volume of the audible indicator 70 is adjustable by a volume control 105 for the comfort of the surgical team and to account for background noise in the usage environment. As explained in greater detail below, when powered, the speaker 70 generates a single fixed tone. The monitor control circuitry 80 pulses the speaker 70 on and off causing the speaker to click to indicate RF current, where the rate of clicking increases as the RF CURRENT signal increases.

Figure 3:
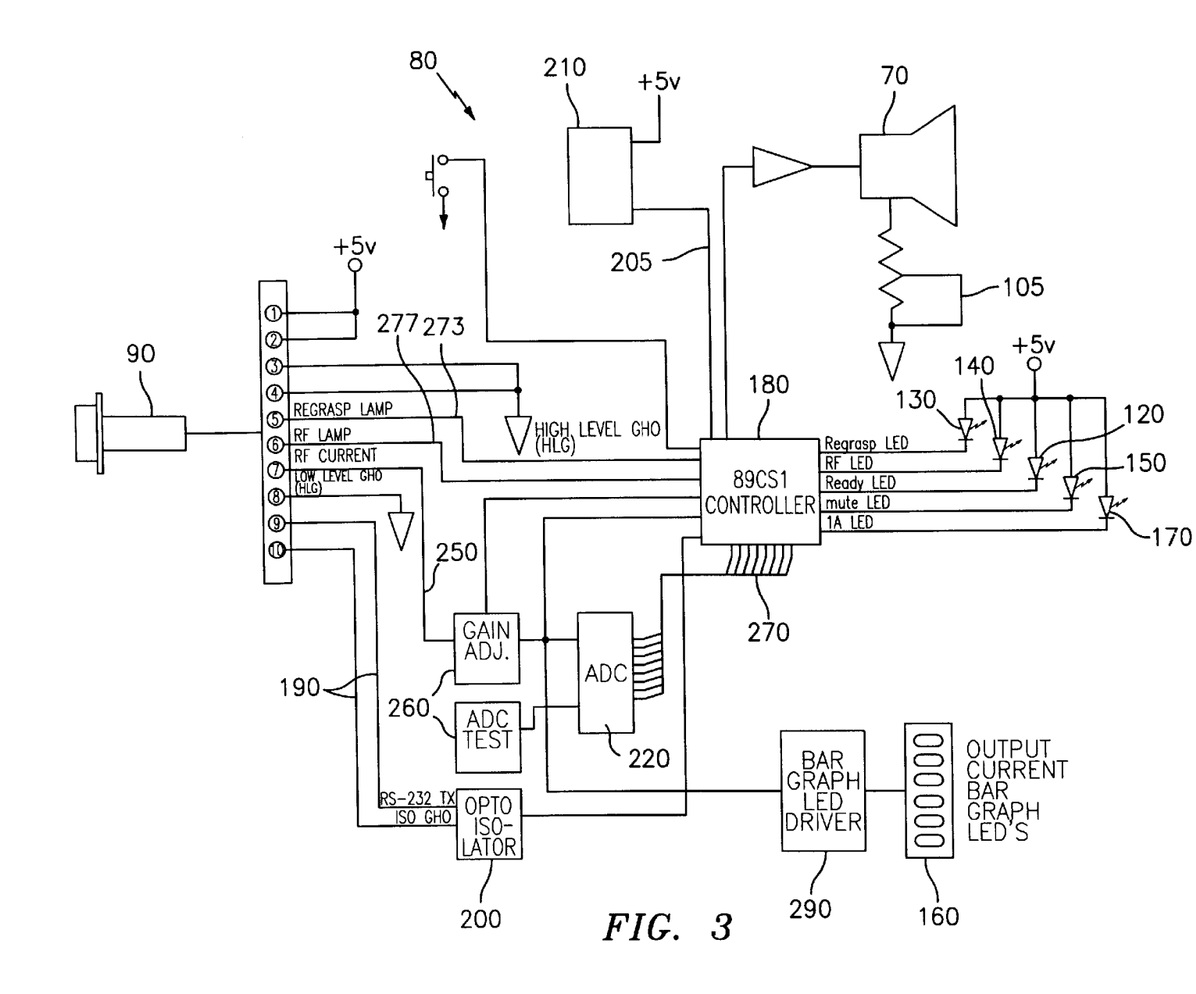
FIG. 3 shows a block diagram of the monitor control circuitry.

In FIG. 3 the monitor control circuitry 80 is shown in block diagram format. The monitor control circuitry 80 receives inputs, and optionally, power, from the electrosurgical generator 20 through the communications link 90. The monitor control circuitry 80 includes a suitably programmed data processor that is preferably implemented as a microcontroller device 180. The microcontroller device 180 has an internal Read Only Memory (ROM), a Random Access Memory (RAM), and a Universal Asynchronous Receiver/Transmitter (UART). A control program for the microcontroller device 180 is stored in the ROM and includes software routines and algorithms for controlling the overall operation of the monitor control circuitry 80. The microcontroller device 180 receives communication signals HOST GENERATOR RS-232 TX and ISOLATED GROUND 190 from the electrosurgical generator 20 (FIG. 1) through an opto-isolator 200 that is connected to the UART internal to the microcontroller device 180.

A watch dog timer 210 monitors the operating power (+5V) received from the electrosurgical generator 20 (FIG. 1) and receives a periodic signal from the microcontroller device 180. The watch dog timer 210 resets the microcontroller device 180 in the event that the power varies beyond a certain level or if the microcontroller device 180 fails to provide the periodic signal.

An analog to digital converter (ADC) 220 receives the RF CURRENT analog input signal 250, scaled by gain adjust circuitry 260, a test signal from internal circuitry 260, and in turn sources a bidirectional digital bus 270 of the microcontroller device 180. It should be noted that the watchdog timer 210 and the ADC 220 can be internal blocks of the microcontroller device 180, and need not be separate, external components.

The microcontroller device 180 has additional digital inputs and outputs organized as a number of ports for receiving the input signals REGRASP 273 and RF LAMP 277 carried by the communications link 90. The microcontroller device 180 input ports also receive an input from mute switch 100 to direct the microcontroller device 180 to mute the speaker 70. An output of the microcontroller device 180 is configured to drive the speaker 70. The volume control 105 for the speaker is preferably implemented as a potentiometer.

Figure 4:
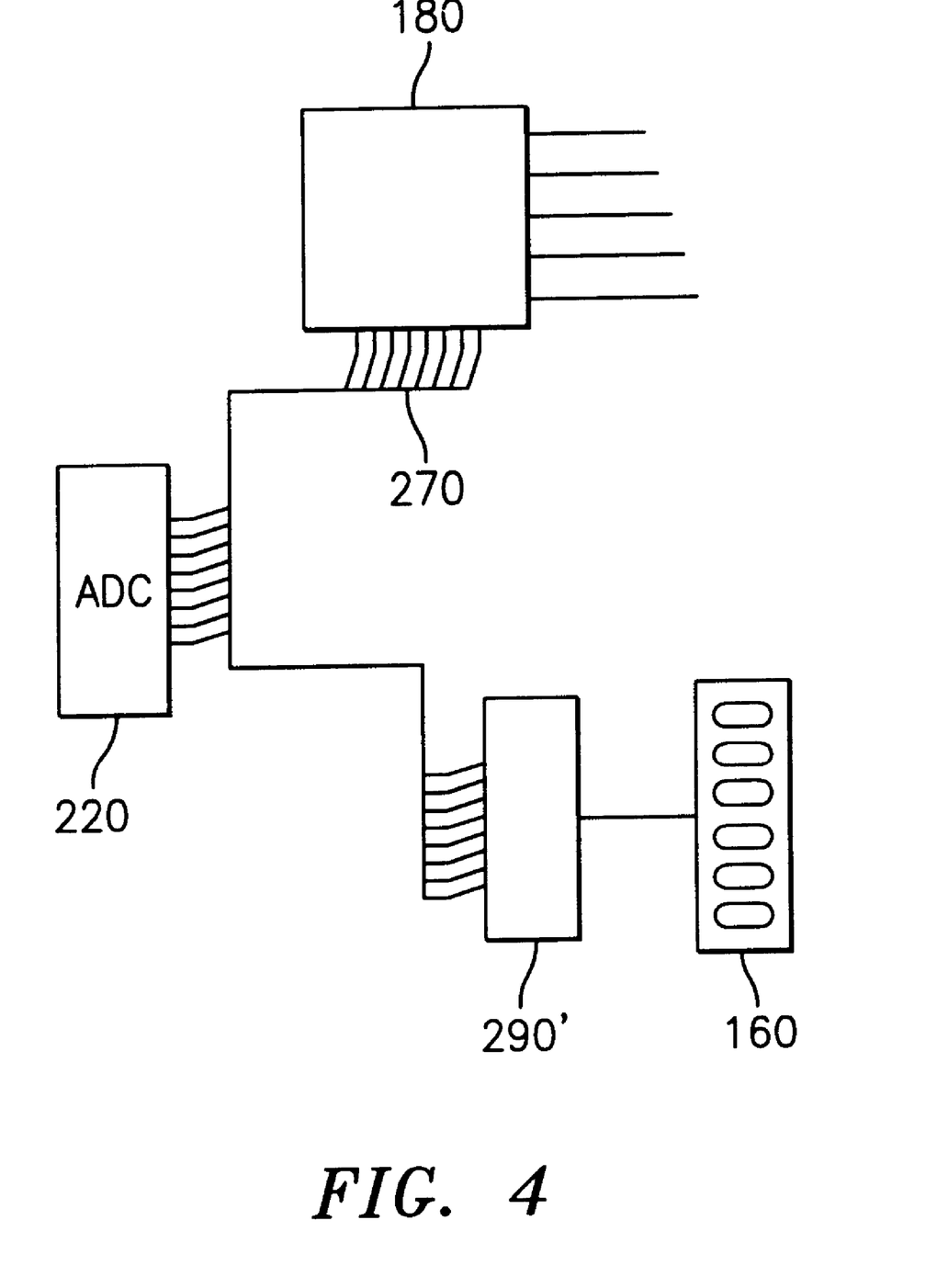
FIG. 4 shows a block diagram of an alternate embodiment of a portion of the RF current display of FIG. 3.

The RF CURRENT analog input signal 250 from the electrosurgical generator 20 (FIG. 1) passes through a gain adjust circuit 260 and is used to drive an input of the ADC 220 and, in this embodiment is also used to drive bar graph LED driver circuitry 290 which in turn drives the 20 segment LED display 160. That is, the LED driver circuitry 290 contains an internal ADC or similar function for converting the input analog (voltage) signal. In an alternate embodiment, shown in FIG. 4, the bidirectional digital bus 270, sourced by the ADC 220, may be used to drive bar graph LED driver circuitry 2901 which in turn drives the 20 segment LED display 160.

Outputs from the microcontroller device 180 also drive the Ready LED 120, Regrasp LED 130, RF LED 140, >1A LED 170, and the Mute LED 150.

Figure 5A:
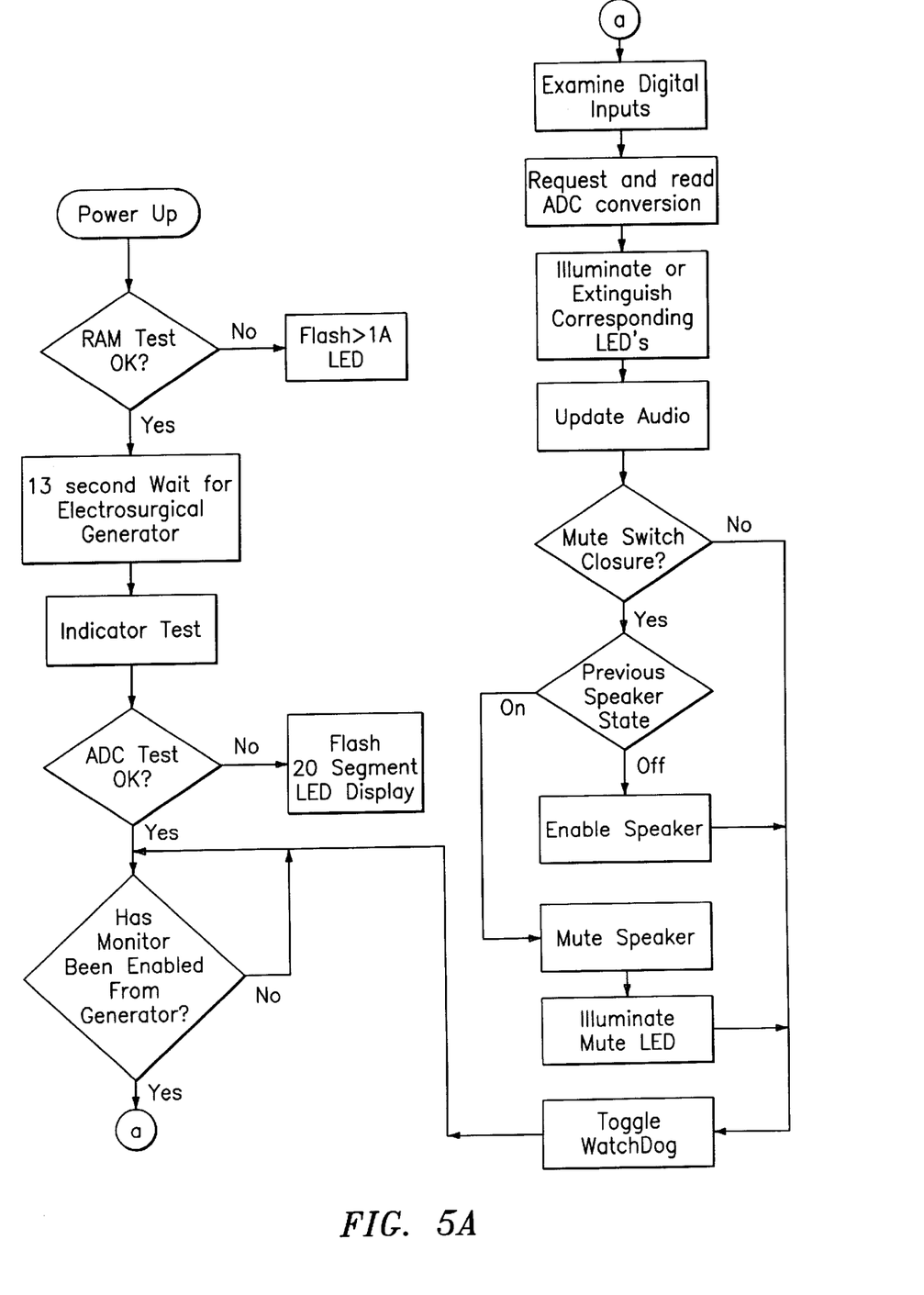
FIGS. 5A and 5B show logic flow diagrams that illustrate the software functions of the monitor.
Figure 5B:
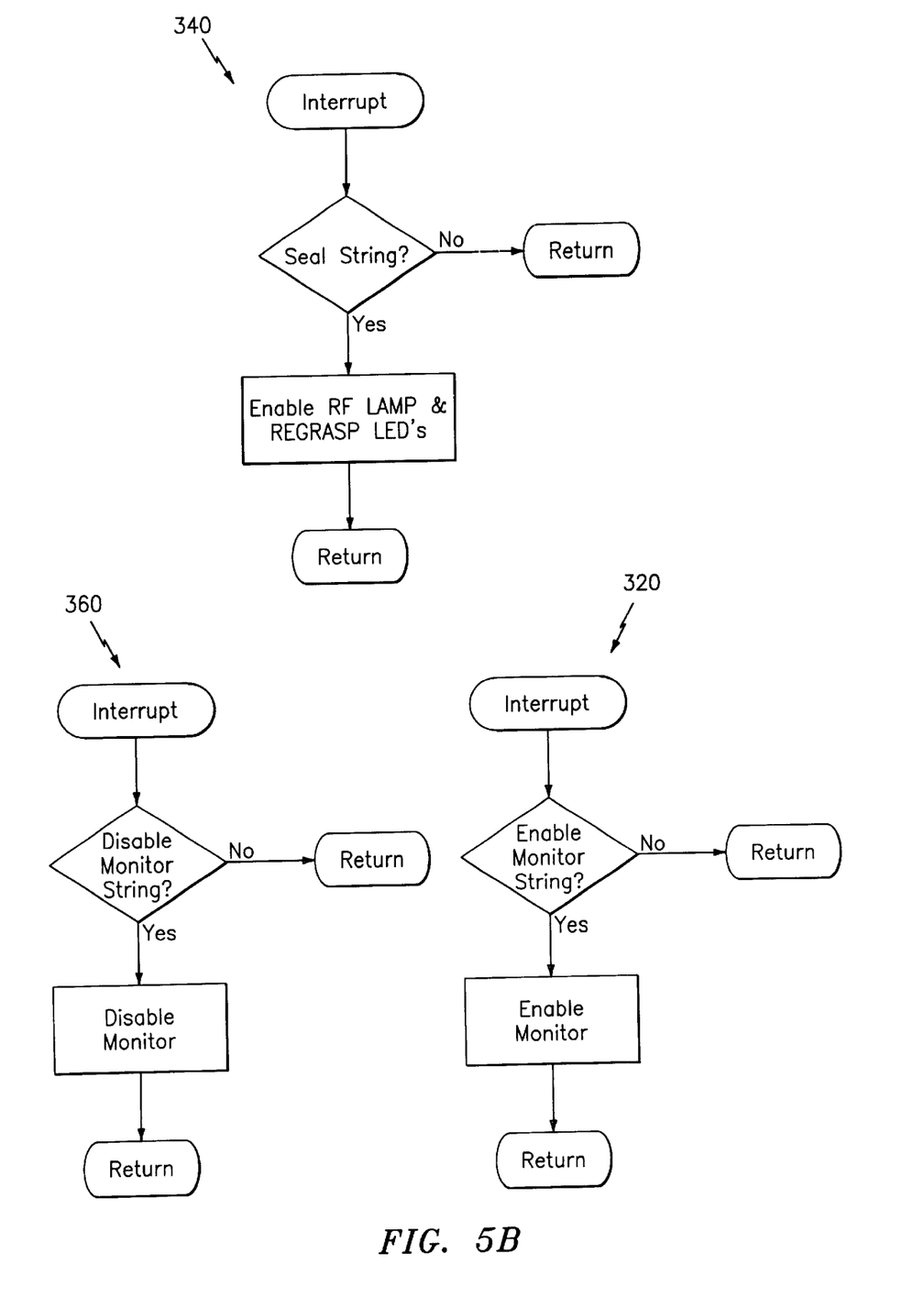

The software algorithms executed by the microcontroller device 180 perform a number of operations that result in the overall control of the monitor 10. Referring now to the logic flow diagram of FIG. 5A, upon application of power to the monitor 10, the microcontroller device 180 executes a power on self test (POST) starting with a RAM test. If the RAM test is unsuccessful, the microcontroller device 180 causes the >1A LED 170 to flash at about 1 Hz. If the RAM test is successful, the monitor waits for 13 seconds to allow the electrosurgical generator 20 to complete its own self test. An indicator test is then executed where all the LED's, the 20 segment LED display 160 and the speaker 70 are energized for about 2 seconds, allowing a user to observe that all indicators are functional. After the indicator test is executed, a test of the ADC 220 commences. If the ADC test is unsuccessful, the microcontroller device 180 causes the 20 segment LED display 160 to flash at about 1 Hz. and extinguishes all other indicators. Upon a successful ADC test, the Ready LED 120 is turned on continuously and the microcontroller device 180 then enables the UART interrupt and waits for an interrupt from the internal UART, indicating that serial communication is being received from the electrosurgical generator 20 (FIG. 1). As shown in FIG. 5B the communication preferably takes three forms.

The electrosurgical generator 20 may send a serial communication simply enabling the monitor 320. In that case the microcontroller assumes that the RF LAMP and REGRASP signals are not provided by the electrosurgical generator and begins the main control program. Alternately, the electrosurgical generator 20 may send a serial communication enabling the monitor and indicating that the electrosurgical generator provides REGRASP and RF LAMP signals 340. In that case the microcontroller enables the RF and REGRASP LED's and begins the main control program. Further, the electrosurgical generator 20 may send a serial communication disabling the monitor 360. In that case the microcontroller returns to the idle state and waits for an enabling communication.

Upon receiving an enabling communication, the microcontroller device 180 begins a main control program by polling the digital signals from the electrosurgical generator 20 (FIG. 1) and requesting the ADC 220 to perform a conversion of the RF CURRENT signal 250. When the conversion is complete, the microcontroller reads it and then preferably causes the speaker 70, if enabled, to click at an increasing or decreasing rate corresponding to an increase or decrease, respectively, of the RF CURENT signal 250. In the preferred embodiment, the RF CURRENT signal 250 is also used to drive the bar graph LED driver circuitry 290. The bar graph LED driver circuitry 290 divides the RF CURRENT signal into 21 different levels and the microcontroller utilizes 21 different click rates that correspond to the 21 different levels. The click rates are predetermined to provide audible distinction as the RF CURRENT signal changes. The microcontroller 180 performs a voltage to click rate conversion by determining which click rate bounds the ADC value. This rate is then used to turn the speaker on and off to create the click. This action is performed once during each loop of the main control program. In other embodiments other audible indicators could be provided, for example, a continuous tone could change in frequency as the RF current increases and decreases.

The microcontroller 180 then causes the LED's on the monitor 10, corresponding to the digital signals from the electrosurgical generator 20, to either illuminate or extinguish. The main control program continues by polling the MUTE switch 190 to detect the event of a switch closure. In response to a closure the microcontroller device 180 examines the state of the speaker 70, making a determination as to whether the speaker 70 is enabled or disabled and then toggling the state. This is most conveniently done by testing a speaker state flag in RAM, and toggling the flag (e.g.: speaker flag=0, speaker muted, speaker flag=1, speaker enabled). Upon toggling the state of the speaker, the microcontroller device 180 toggles the signal line 205 to the watch dog timer 210 and loops back to the beginning of the main control program. If no switch closure is detected, the microcontroller device 180 also then toggles the signal line 205 to the watch dog timer 210 and loops back to the beginning of the main control program.

Thus a method is disclosed for providing indications corresponding to input signals from an electrosurgical generator, the indications being remotely indicated from the electrosurgical generator, comprising the steps of:

operating a remote monitoring device to receive input signals from the electrosurgical generator; and receiving an enabling communication, and in response to the enabling communication, controlling a plurality of indicators of the remote monitoring device in response to the input signals in order to provide an operator with knowledge of an operational status of the electrosurgical generator.

The invention also contemplates an embodiment where the step of controlling is initiated after a receipt of a predetermined validation code from the electrosurgical generator.

It should be noted that certain of the indicators could be eliminated. For example, the LED display 160 could be removed, and the audible indicator used as the sole indicator of RF current, and vice versa.

While the invention has been particularly shown and described with respect to preferred embodiments thereof, it will be understood by those skilled in the art that changes in form and details may be made therein without departing from its scope and spirit.

What is claimed is:

1. A monitor for an electrosurgical generator, comprising:
a communication link for remotely locating the monitor from said electrosurgical generator;
an input port for receiving input signals from said electrosurgical generator through said communication link;
a plurality of indicators; and
control circuitry for controlling said plurality of indicators in response to said input signals to provide an operator with an indication of the operational status of the electrosurgical generator,
wherein said control circuitry is enabled by at least one of a plurality of digital communications received through said communication link from said electrosurgical generator.

2. The apparatus of claim 1 further comprising at least one audible indicator wherein said control circuitry is responsive to input from an operator to mute said audible indicator and for energizing a predetermined visual indicator for indicating that said audible indicator has been muted.

3. The apparatus of claim 1 wherein at least one of said signals from the electrosurgical generator indicates the state of an indicator on said electrosurgical generator.

4. The apparatus of claim 1 wherein at least one of said signals from the electrosurgical generator indicates a magnitude of an RF current being generated by the electrosurgical generator.

5. The apparatus of claim 4, wherein said plurality of indicator comprise visual indicators further comprising a multi-element display responsive to said at least one signal that indicates a magnitude of an RF current.

6. The apparatus of claim 2 wherein said control circuitry further operates to controllably energize said audible in response to an input signal indicating a magnitude of an RF current output from the electrosurgical generator.

7. The apparatus of claim 1, wherein said communication link is a wireless link.

8. The apparatus of claim 1, wherein said communication link is an optical link.

9. The apparatus of claim 1, wherein said one of a plurality of digital communications is in the form of a digital bit stream.

10. The apparatus of claim 1, wherein said one of a plurality of digital communications indicates that said electrosurgical generator provides certain optional signals as part of said input signals.

11. A method for providing indications corresponding to input signals from an electrosurgical generator, said indications being remotely indicated from said electrosurgical generator, comprising:

operating a remote monitoring device to receive said input signals including a plurality of digital communications from said electrosurgical generator; and receiving at least one of said plurality of digital communications including an enabling digital communication from said electrosurgical generator and, in response to said enabling digital communication, controlling a plurality of indicators of said remote monitoring device in response to said input signals to provide an operator with knowledge of an operational status of said electrosurgical generator.

12. The method of claim 11 wherein said plurality of indicators comprise at least one audible indicator, further comprising the steps of:

muting said audible indicator in response to input from an operator to mute said audible indicator and energizing a predetermined visual indicator for indicating that said audible indicator has been muted.

13. The method of claim 11 further comprising the step of:
controlling at least one of said plurality of indicators in order to indicate the state of an indicator on said electrosurgical generator.

14. The method of claim 11 wherein said input signals from the electrosurgical generator further comprise at least one signal indicating a magnitude of an RF current being generated by the electrosurgical generator, further comprising the step of:

visually indicating a magnitude of the RF current being generated by the electrosurgical generator in response to said at least one signal indicating the magnitude of the RF current.

15. The method of claim 11, wherein said one of a plurality of digital communications is conveyed over a wireless link.

16. The method of claim 11, wherein said one of a plurality of digital communications is conveyed over an optical link.

17. The method of claim 11, wherein said one of a plurality of digital communications is in the form of a digital bit stream.

18. The method of claim 11, wherein said one of a plurality of digital communications indicates that said electrosurgical generator provides certain optional signal as part of said input signals.

* * * * *